United States Patent [19]

Davis et al.

[11] Patent Number: 5,610,077

[45] Date of Patent: Mar. 11, 1997

[54] PROCESSES AND APPARATUS FOR CARRYING OUT SPECIFIC BINDING ASSAYS

[75] Inventors: Paul J. Davis, Bedfordshire; Philip Porter, Bedford, both of England

[73] Assignee: Unilever Patent Holdings B.V., Rotterdam, Netherlands

[21] Appl. No.: 275,755

[22] Filed: Jul. 19, 1994

Related U.S. Application Data

[63] Continuation of Ser. No. 744,658, Jun. 14, 1985, abandoned, which is a continuation of Ser. No. 348,048, filed as PCT/GB81/000107, Jun. 22, 1981 published as WO82/00058, Jan. 7, 1982, abandoned.

[30] Foreign Application Priority Data

Jun. 20, 1980 [GB] United Kingdom ................... 8020160

[51] Int. Cl.$^6$ .................................................. G01N 33/53
[52] U.S. Cl. ........................... 436/518; 436/807; 436/80
[58] Field of Search ................................ 435/7.92, 7.94; 436/518, 524, 528, 807, 810

[56] References Cited

U.S. PATENT DOCUMENTS

| | | |
|---|---|---|
| 3,654,090 | 4/1972 | Schuurs et al. . |
| 3,791,932 | 2/1974 | Schuurs et al. ........................ 435/7.9 |
| 3,867,517 | 2/1975 | Ling . |
| 4,016,043 | 4/1977 | Schuurs et al. . |
| 4,098,876 | 7/1978 | Piaso et al. . |
| 4,146,365 | 3/1979 | Kay et al. ............................. 435/7.9 |
| 4,234,316 | 11/1980 | Hevey ...................................... 422/68 |
| 4,244,940 | 1/1981 | Jeong et al. ............................. 422/61 |
| 4,258,001 | 3/1981 | Pierce et al. ............................. 435/805 |
| 4,361,647 | 11/1982 | Remington et al. ..................... 435/7.9 |
| 4,376,110 | 3/1983 | David et al. ............................. 436/513 |
| 4,690,890 | 1/1987 | Loov et al. ............................. 436/531 |

FOREIGN PATENT DOCUMENTS

0045103 2/1982 European Pat. Off. .
2074727 11/1981 United Kingdom .................. 435/7

OTHER PUBLICATIONS

Nippon Rinsho, vol. 34, No. 6 (1976) pp. 1274 to 1279 (H. Hirai).

Sevier et al, "Monoclonal Antibodies in Clinical Immunology," Clin Chem., vol. 27, No. 11 (1981) pp. 1797–1806.

Steensgaard et al, Chemical Abstracts, 94:81866c, p. 535 (1981).

Flamand et al, "Use of Hybridoma Monoclonal Antibodies in the Detection of Antigenic Differences Between Rabies and Rabies-related Proteins. I. The Nucleocapsid Protein". J. Gen. Virol. 48 (May 1980) 97–104.

Steensgard et al, "The development of difference turbidimetric analysis for niroclonal antibodies to human IgG., " Mol. Immunol. 17(1980) 1315–1318.

(List continued on next page.)

*Primary Examiner*—Toni R. Scheiner
*Attorney, Agent, or Firm*—Cushman, Darby & Cushman, L.L.P.

[57] ABSTRACT

A process for carrying out a specific binding assay by reacting (a) a sample under assay for the possible presence of a substance being tested for, (b) a specific binding partner for the substance being tested for, immobilised on a solid support, and (c) a specific binding partner for the substance being tested for which is conjugated to a detectable marker, to thereby form a complex by reacting between whatever quantities are present of the substance being tested for in (a) with reagents (b) and (c). The marker is immobilised to the support via the substance being tested for, and is detected or assayed as an index of the quantity present in the sample (a) of any of the substance. The reaction ingredients (a), (b) and (c) are all mixed in a single step for reaction in a single reaction liquid. Competitive interference between the binding reactions of the substance being tested for and reagents (b) and (c) is avoided by use of monoclonal antibodies of narrow and different, non-interfering specificity, reaction reagent (b) is immobilized on the surface of a displacer body.

2 Claims, 3 Drawing Sheets

OTHER PUBLICATIONS

Wikfor et al, "Use of Monoclonal Antibodies in Diagnosis of Rabies Virus Infection and Differentiation of Rabies and Rabies–Related Viruses," J. Virol. Methods 1 (Mar. 1980) 33–46.

Flamand et al, "Use of Hybridomo Monoclonal Antibodies in the Detection of Antigenic Differences Between Rabies and Rabies–related Virus Proteins. II. The Glycoprotein" J. Gen. Virol. 48(May 1980) 105–109.

Cuello et al, "Detection of substance P in the central nervous system by a monoclonal antibody", Proc. Nat'l. Acad. Sci. USA, 76(1979) 3532–6.

PROCESSES AND APPARATUS FOR CARRYING OUT SPECIFIC BINDING ASSAYS

This is a continuation of application Ser. No. 06/744,658, filed on Jun. 14, 1985, which was abandoned upon the filing hereof which was a continuation of application Ser. No. 06/348,048, filed as PCT/GB81/00107, Jun. 22, 1981 published as WO82/00058, Jan. 7, 1982, now abandoned.

This invention relates to processes for carrying out specific binding assays, e.g. immunoassays, and to apparatus, e.g. test kits, for carrying out these processes.

In particular embodiments the invention is applicable to enzyme-linked and fluorescent-marker-linked specific binding assays, including immunoassays.

A wide variety of immunoassays and other specific binding assays is already known.

Examples of such assays and the materials used for them are given in S. Spector, Ann.Rev.Pharm. (1973) 13, 359–70 (radioimmunoassays), L. E. M. Miles and C. N. Hales, Nature (1968) 219, 186–189 (assays using radioactive, enzyme and other markers), E. Habermann, z.klin.Chem.u.klin.Biochem. (1970) 8, 51–55 (radioactively-labelled and enzyme-labelled assay procedures), and in G.B. patent specification No. 1,363,565 (enzyme-labelled immunoassays) and U.S. Pat. Nos. 4,150,949 and 4,160,818 (fluorescence-labelled immunoassay).

An important group of such assays comprises those in which a ternary complex is formed between a specific adsorbent, the material under assay, and a marker conjugated material with specific binding capacity for the material under assay ("conjugate"). Certain assays of this kind have been called "sandwich" or "antiglobulin" assays. They have the property that the quantity of marker becoming fixed to the specific adsorbent is directly rather than inversely related to the quantity of the material under assay that participates in the ternary complex, and this can be simply measured after separation of the immobilised material from the remaining free marked conjugate, in whatever manner is appropriate to the marker in use.

However, as appears for example from the above-mentioned Habermann (1970) publication and G.B. specification No. 1,363,565, the performance of these assays is not without difficulty: they demand either a number of successive manipulation steps to carry out the assay reactions, or else suffer from low sensitivity, which careful choice of reagents has not so far been able to overcome.

Commercial test kits are available comprising essentially:

(a) a plate consisting of an array of tubes or pre-formed wells which are coated with an antibody or antigen as the case may be;

(b) an enzyme linked to an appropriate antibody (a so-called conjugate) against a substance to be detected if present in a test sample and (c) a substrate for the determination of the activity of the enzyme.

One standard procedure for conducting an assay for antigen or antibody involves:

(1) determining the working dilution for the test sample;

(2) removing any excess of antibody or antigen used to sensitise the wells;

(3) washing the wells;

(4) introducing a proportion of the suitably diluted test sample;

(5) incubating for about two hours to allow the substance to be detected in the test sample to bind to the sensitising substance;

(6) washing the wells to remove unreacted material;

(7) introducing the suitably diluted conjugate (incubate for about 2 hours);

(8) washing the wells to remove unreacted material;

(9) adding a solution of the substrate;

(10) incubating until a suitable intensity of colour develops as a result of the reaction of the substrate with the enzyme;

(11) stopping the reaction, e.g. with a strong alkali: and (12) measuring the optical density of the reacted substrate solution.

This procedure is also time-consuming since each of the several antibody/antigon reactions requires several hours to reach equilibrium. In practice, shorter incubation times are used but only at the expense of sensitivity and/or economy.

According to the results of the present work, it is believed that an obstacle to the use of fewer assay steps is an unwanted interference with the formation of the desired immobilised complex which can originate in interfering reactions between two of the components. By using a specific binding agent of selected narrow specificity, or in slow-release form, such interference can be avoided, and high-sensitivity assays carried out using fewer manipulation steps.

According to this invention there is provided a process for carrying out a specific binding assay (for example an immunoassay) in which (a) a sample under assay, possibly containing a substance being tested for, is reacted with (b) a specific binding partner for the substance being tested for, immobilised on a solid support, and (c) a specific binding partner for the substance being tested for which is conjugated to a detectable marker, thereby to form a complex by reaction between whatever quantities are present of the substance being tested for with reagents (b) and (c), in which the marker is immobilised to the support via the substance being tested for, and is detected or assayed as an index of the quantity present in the sample (a) of any of the substance being tested for; characterised in that reaction ingredients (a), (b) and (c) are all mixed in a single step for reaction in a single reaction liquid, and competitive interference between the binding reactions of the substance being tested for and reagents (b) and (c) is avoided either by use of an antibody of narrow specificity, such as a monoclonal antibody, to avoid the interference, or by use of a slow-release form of reagent (c).

The narrow specificity required of the antibody is a capacity to bind specifically with the substance under test but without preventing the binding reaction between the substance under test and its other specific binding partner. Such an antibody can be selected out of a number of antibodies with an affinity for the substance under test, by using normal methods to verify the progress of a binding reaction between the other specific binding partner and a complex previously formed between the substance to be tested in the assay and the narrow-specificity antibody to be selected.

According to a preferred embodiment of the present invention, the conjugate between antibody and the enzyme or other marker, and/or the antibody (if any) which is coupled to the solid surface, comprises a monoclonal antibody or other antibody of sufficiently narrow specificity to ensure that the desired assay reaction or reactions are not impeded by competition between the conjugate and the immunosorbent in their reactions with whatever quantities are present of the substance being tested for in the sample under assay. Monoclonal antibody of sufficiently narrow specificity can, for example, be produced as antibody derived from a line of antibody-producing cells, derived from a single antibody-producing progenitor cell or cells. Such a line can, for example, be produced by known cell fusion, culture and isolation techniques using very pure antigens as comparative material.

Alternatively, in many cases antibody of sufficiently narrow specificity can be obtained in the (polyclonal) immunoglobulins of antisera raised against discrete chemical or physical molecular fragments of the material under test, for example, antibody against Fc fragments (or against smaller peptide fragments) of immunoglobulins to be tested for, or against sub-units or peptides of protein antigens to be tested for. The object in each case is to ensure substantial freedom from interference which can arise particularly, for example, in carrying out immunoassays of the "sandwich" or "antiglobulin" test configurations.

In a "sandwich" test configuration, antigen under test can be specifically adsorbed to a first antibody bound to a solid surface, and a second antibody carrying an enzymic or other (e.g. fluorescent or radioactive) marker is specifically bound to the adsorbed antigen under test. Marker specifically so bound is used for measurement and determination of the antigen under test, e.g. by direct measurement, such as radiometry or fluorimetry, or exposure of enzyme marker to substrate followed by product measurement. Thus, in preferred sandwich tests, the two antibodies used can have different, non-interfering specificity with respect to the same antigen under test.

In an "antiglobulin" test configuration, sometimes also referred to as a "sandwich" test configuration, the position is analogous: the material under test is itself an immunoglobulin; the material bound to a solid surface is its corresponding antigen or hapten; and the material carrying the marker is an antiglobulin corresponding to the species and immunoglobulin type of the antibody under test. In preferred antiglobulin tests, the antiglobulin can have sufficiently narrow specificity as not to interfere with the subsequent adsorption of its corresponding globulin to the insolubilised antigen.

If antibodies from ordinary antisera raised against unmodified antigen (polyclonal antibodies) are used in sandwich or antiglobulin tests, there is a very likely risk that if all ingredients are mixed in a single step there will be interference between the two specific adsorption reactions. When such tests are carried out according to the present invention, using apparatus as described herein, such interference can be avoided either by using antibodies of narrow specificity as described, or else by ensuring that the binding of test material to the solid surface takes place before exposure of test material to the other (marker-conjugated) binding agent if there is a risk that binding by that other agent would prevent subsequent adsorption to the solid surface. Such a sequence can be ensured by arranging for slow release of the other (marker-conjugated) binding agent.

Particular instances of suitable assay specificities, antibody specificities, and slow-release forms of conjugated reagent (c) are described for example below.

It has also been found that in carrying out such specific binding assays, a worthwhile improvement in reaction kinetics can be obtained if the reaction liquid containing ingredients (a), (b) and (c) is contained in a well or cup of which the majority of the volume is occupied by a displacer body. (The use of inserts of various rod or ball shaped forms is known in connection with other kinds of immunoassay, as described in G. B. Specification Nos. 1,414,479 and 1,485,729.)

The displacer body can, for example, be of a shape substantially complementary to and slightly smaller than that of the cup or well, so that the liquid phase containing one of the specific binding reagents is approximately in the form of a shell occupying the space between the displacer and the cup or well. The displacer can be loose-fitting and not fixedly mounted, i.e. movable relatively to the cup or well, so that by relative motion between displacer and well the liquid between them can be given a stirring or agitation motion.

For example, a round well can have a round displacer therein with an external diameter slightly smaller than the diameter of the well. The presence of the displacer can reduce the space available for liquid in the well by a factor of for example 2–10, e.g. 3–8, comparing volumes based on similar liquid levels in the well, e.g. when filled to its normal operating level, or its maximum capacity. For example, a microtitre well designed to have 300 microlitre of liquid filled into it during a normal assay, can be used with a displacer leaving 30–150 microlitre liquid space, e.g. 50–100 microlitre.

The use of wells or cups together with displacers as described herein can improve the efficiency of the assay reaction steps because, in the first place, it allows more concentrated reagents to be used with no increase in the weight of reagent or decrease in the size of the microtitre wells, compared with the normal conditions encountered in microtitre wells of given size; and in the second place, it increases the sensitised surface area available to react with a given liquid reagent volume, so that comparatively faster adsorption kinetics can be achieved without having to increase specific reagent density on the sensitised surface or encountering problems of crowding.

A set of displacer bodies can be preferably present in certain embodiments of the invention, e.g. as an integral part of a lid which can be fitted onto a microtitre plate, e.g. a standard plate of 8×12 wells. The set can be large enough to fit all wells of the plate or a sub-set thereof, e.g. a row. The dimensions of the displacers and the volume of liquid to be dispensed into the well can be chosen relative to the well in the manner described above, and preferably so that the liquid to be tested is in contact with substantially the major part and preferably the whole inner surface of the well.

The immobilised specific binding partner (reagent (b)) for the substance to be assayed can be immobilised on the wall of the well or cup in which the assay reaction takes place. Alternatively, according to a feature of the invention independently capable of providing advantage and convenience in use, a liquid displacer, for example in the form of a stick, peg or stud, for dipping into a liquid assay reagent, can have an immunosorbent surface. This allows the portion of the assay materials needing to be carried over from one reagent to the next, and the associated manipulations, to be handled more easily than when the sensitised surface is part of a hollow well. An alternative form for such a liquid displacer body is a tuft of bristles or leaves of suitable material, or equivalent body with large surface area. A further alternative form is a stud or peg with relatively hollowed-out and projecting portions of its surface, e.g. with grooves and associated ribs, e.g. annular grooves. Such an arrangement can give robustness, increased sensitised surface area, and better reactivity.

Test apparatus according to related embodiments of the invention can thus comprise a set of sensitised liquid-displacer bodies of one or more of such forms, joined to a common handling-bar, link or lid, and for use in combination with a complementary set or sets of wells containing any of the remaining materials used in the assay. The several displacer bodies of the set can have the same or different sensitisation so that one or a plurality of different assay types can be carried through simultaneously. If desired, the displacer bodies can be removably and exchangeably mounted on the handling bar, link, or lid, so that sets of desired specificity can be built up at will from a common stock for carrying out large numbers of tests according to a desired pattern.

One advantage of such arrangements is that a number of displacer bodies can be sensitised in the same body of liquid ragent, avoiding fluctuating conditions of concentration, etc., resulting from dosing aliquots into wells.

The displacer bodies can, in this embodiment, be of any material suitable for the preparation of an immunosorbent by covalent bonding or adsorption: e.g. polystyrene, nylon, or cellulose acetate. (The nature of the displacer surface does not matter provided it is inert, when the sensitisation is to be on the well surface rather than the displacer surface.) Linkage of antibodies, antigens, etc., to the displacer bodies can be carried out by linking methods known in themselves, e.g. partial acid hydrolysis of nylon surface, substitution of exposed amine surface with glutaraldehyde, and coupling of material to be bound, e.g. antibody or antigen to immobilised aldehyde groups. Suitable methods among a wide variety are given for example by Inman & Hornby (1972) Biochem. J. 129, 255; Campbell, Hornby & Morris (1975) Biochim. Biophys. Acta 384, 307; Mattiasson & Nilsson (1977) F.E.B.S. Letters 78, 251; and G.B. patent specifications Nos. 1,470,955 and 1,485,122.

It can be seen that the invention also provides a kit of test materials for carrying out a specific protein-binding assay, comprising (i) an immobilised specific binding partner for a substance to be tested for, carried on a solid support, and (ii) a marker-conjugated specific binding partner for the substance to be tested for, which can be added to a reaction liquid contacting immobilised reagent (i) either as a slow-release form, or in any form provided that the specific binding partners in reagents (i) and (ii) include an antibody of narrow specificity so that reagents (i) and (ii) do not interfere with each other's binding reactions with the substance to be tested. Optionally the kit can also comprise materials for later estimation of the amount of marker immobilised during the assay.

Reagent (i) can be immobilised on either a displacer body for a reaction well, or on a reaction well wall, as described above. A slow-release form of reagent (ii) can be for example a sucrose or equivalent glaze on a complementary surface of either the displacer or the well wall, also as described above. The narrow-specificity antibody can be selected for example from monoclonal antibodies in the manner already described.

The invention is further illustrated by reference to the following details and accompanying drawings, of which.

Figure 1:
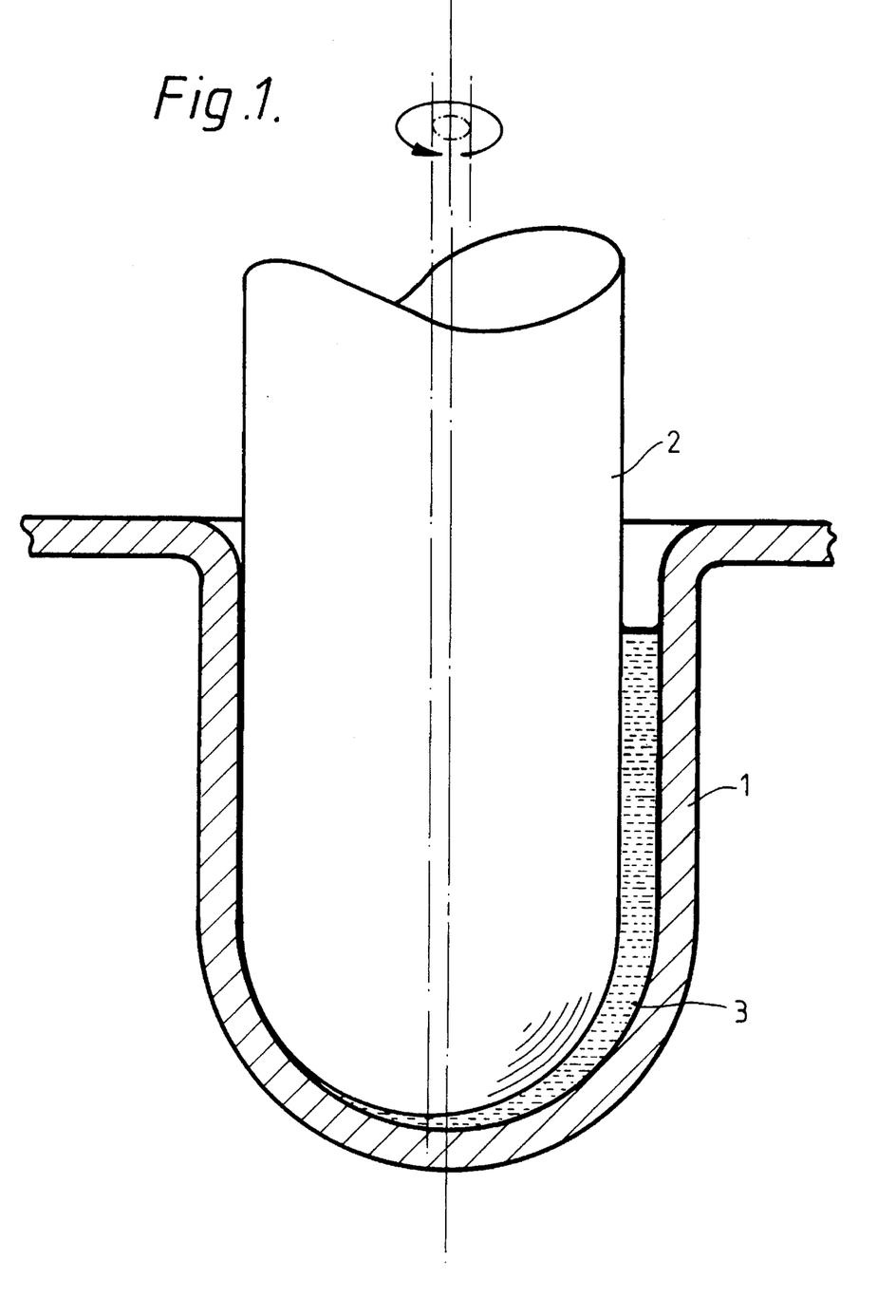
FIG. 1 is a vertical cross-section of an arrangement of container and displacer for carrying out specific binding assays according to the invention.

FIG. 1 of the drawing shows in vertical cross-section a round-bottom plastics microtitre well-shape vessel 1 containing a round-section round-bottom displacer body 2 of slightly smaller and complementary shape. The displacer 2 can be of glass or plastics material. The normal capacity of well 1 is for a 300 microliter sample. The presence of the displacer 2 reduces the effective capacity to 50 microliter. This quantity of liquid 3 forms a shell in contact with the whole of the surface area of the normal capacity of the well and with the displacer body 2. Thus the surface-to-volume ratio of liquid 3 is several times greater than that of the body of liquid which would fill the normal capacity of the well in the absence of displacer 2.

Displacer 2 can be left loose so that during use of the well for assay any agitation given to the well 1 causes stirring of liquid 3. Alternatively, displacer 2 can be directly driven. In one arrangements, shown in FIG. 2, a tray 4 containing a 2-dimensional array of wells similar to well 1 has a lid 5 to which a complementary set of displacer bodies similar to cisplacer 2 is mounted the displacers may be integrally formed with lid 5, e.g. in the form of hollow moulded protrusions. In an alternative arrangement the fixed set of displacers may form a row or rows only, less than the full array.

In use, for example, for immunoassay of the ELISA type, the bottoms and lower parts of the walls of wells 1 are coated with immunological reagent to form immunosorbent, and 50 microliter quantities of the materials under test, in suitable dilutions and media, are contacted with the well walls and bottoms, by the use of the displacer bodies 2. Immunological reagent conjugated to enzyme marker, if not already dispersed throughout the reaction liquid, is added to the reaction liquid in an alternative way: The displacers can be coated with a conjugate of a detectable enzyme or other marker with an immunological reagent, e.g. antigen or antibody. Suitable quantities of the conjugate can be dried onto the tips of the displacer bodies, preferably in a glaze, e.g. of sucrose, to prevent aggregation of conjugate molecules and ensure a gradual and slow solubilisation of the conjugate thereby avoiding saturation of the immunosorbent with the conjugate before the former gets the chance to react with the substance to be detected. The test is then performed by dispensing an appropriate volume of test sample consisting, for example, og patient's serum into a well, followed by inserting a displacer body into the well. Thus, the sample and conjugate can be added almost simultaneously, thereby reducing the time-consuming sequence of operations. After the slow release of the conjugated material from the dried glaze on the tips of the displacers 2, formed for example, by evaporation of a solution of the conjugate and sucrose, (or after formation of the assay complex from predispersed reagents) the amount of specifically bound enzyme marker is measured in the usual way. The dosimetry and quantitation of the reagents for the test are carried out according to well-established methods and in themselves form no part of the invention.

Figure 3:
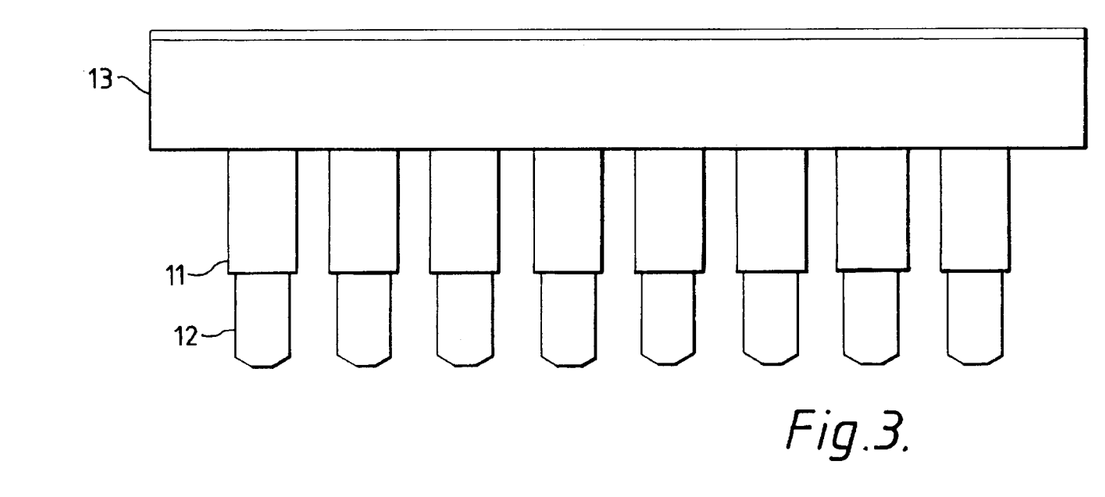
FIGS. 3 and 4 show in diagrammatic side view and part-sectional end view, an assembly of displacers for carrying out certain embodiments of the invention.
Figure 4:
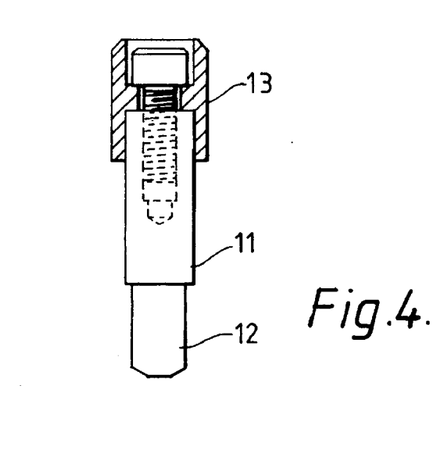

FIGS. 3 and 4 of the accompanying drawings show, in diagrammatic side view and end (part-sectional) view, an assembly of displacer bodies for carrying out specific binding assays according to a further and advantageous arrangement given by way of example. The assembly of such displacer bodies can form part of composite apparatus according to the invention comprising such an assembly (or a single such displacer according to the invention) together with a complementary well or wells for carrying the liquids used in the assays. Either (preferably) the displacer, or the well, carries immobilised specific binding agent.

Referring to FIGS. 3 and 4, the characteristic component of the apparatus for carrying out the assay in each well is a liquid displacer 11 in the form of a stud, stick or peg as shown for dipping into liquid in an assay well as described herein. The displacer 11 is formed, e.g. by moulding or turning in a suitable material such as nylon, cellulose acetate or polystyrene. One preferred form is a nylon peg, of for example, about 5 mm greatest diameter, or slightly narrower than the internal diameter of an associated microtitre well, and about 15–20 mm height to project out of such a well. About, for example, 8 millimeter of a lower extremity 12, or other lower portion of displacer 11, can conveniently be provided with grooves, a screw thread, chamfering, or other irregularity to increase its surface area, not shown in detail in the drawings, which in FIGS. 3 and 4 indicate only a slight overall narrowing of grooved extremity 12 of displacer 11 due to the formation of such grooves.

Figure 2:
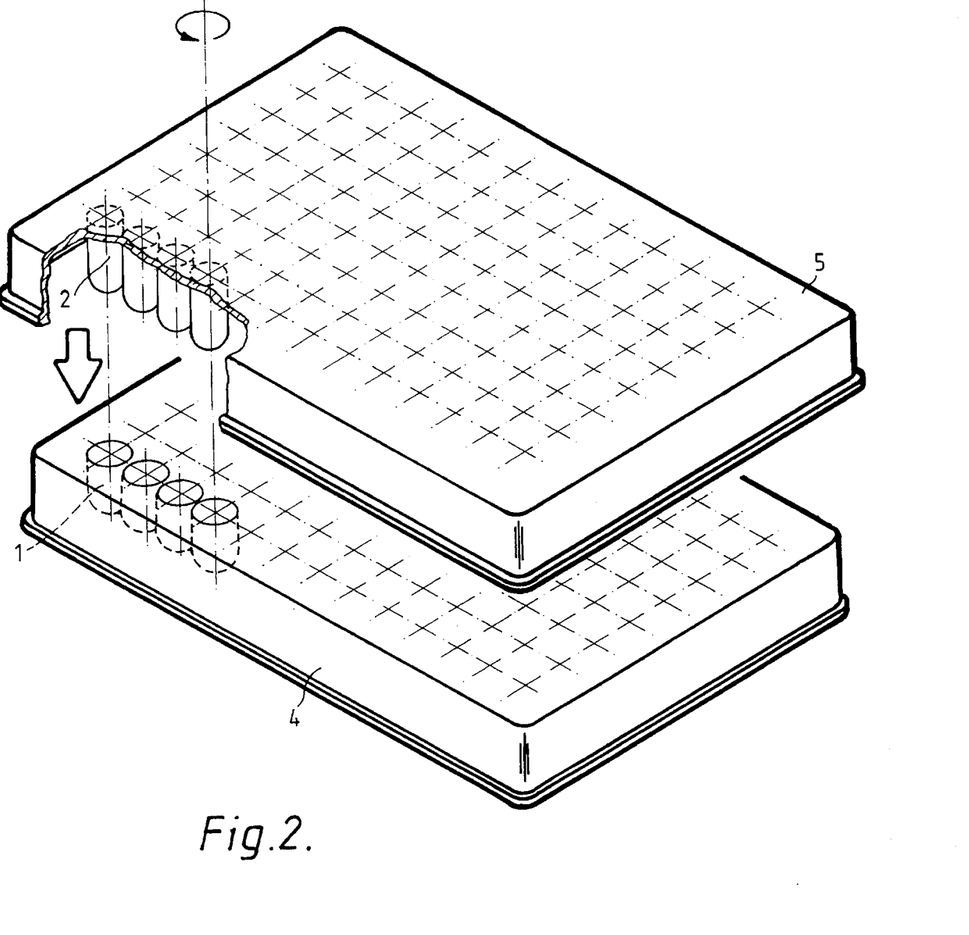
FIG. 2 diagrammatically shows an array of several of the arrangements shown in FIG. 1.

Each displacer 11 is mounted on a handling piece 13 which can have either one displacer 11 or as many as desired mounted thereon, e.g. in a one-dimensional array, as shown, or a two-dimensional array, corresponding to the arrangement of FIG. 2. The displacers 11 can be formed either as one piece with the handling piece or as separate mountable parts which can, if desired, be exchangeable. Illustrated is a socket-and-screw arrangement for exchangeably mounting displacers 11 of the type described at, for example, about 9 millimeter intervals, corresponding to well spacings in the complementary microtitre plate. The handling piece can be of any suitable material, e.g. plastics such as nylon, etc., or metal, e.g. brass, copper or stainless steel.

Biological/chemical conditioning of the displacer 11, e.g. the lower grooved extremity 12 thereof, can be carried out for example as follows to suit the material for carrying out specific binding assays such as immunoassay. The displacer can, if desired, be used as described in Example 1, but alternatively and preferably, it can be made to carry an immunosorbent or other specific binding adsorbent. Antibody or antigen, for example, of type suitable for the desired assay configuration which in itself forms no part of this invention, can be attached by physical adsorption (especially when using polystyrene) or (preferably) by covalent linkage to grooved extremity 12, e.g. by methods already referred to herein.

The assay is then carried out, for example, as follows. Reagent and/or test solution is placed in the well, to a volume sufficient to fill the well only when the displacer is inserted (50–200 microliter for example). With the displacer present the binding reactions take place, and washing can be achieved simply by removing the displacers and rinsing them, e.g. under running tap water.

Even though two binding events may be required (e.g. test antibody binds to immobilised antigen, then enzyme-conjugated antiglobulin binds to the test antibody) it is possible to complete the binding sequence in a single step. This requires the careful choice of reagents, as described above, so that the conjugate antibodies do not compete for all the binding sites on the test material and prevent it from binding to the immunosorbent.

The presence of the displacers in the wells can provide for the important operation of stirring the fluid samples. Not only does this allow a more rapid binding reaction, it also allows the conjugate to be pre-dried into the wells in a firm and stable state, such that it can only be reconstituted by means of such stirring. The stirring might be continued for the duration of the whole binding step, or might be started only after the first binding reaction has been completed. A suitable form of coating is for the well bottoms to be given a dried sucrose glaze containing the conjugate. This can release slowly enough to achieve the desired sequence of binding reactions, as discussed herein above.

After the binding reactions have been completed the displacers can be washed and transferred to another set of wells containing a solution of enzyme substrate, where they remain until the positive controls have developed an adequate colour (and negative controls are still adequately blank). In a standard ELISA, the enzyme/substrate reaction has to be stopped by adding a reagent such as 2M sodium hydroxide solution, but even this step can be dispensed with when the arrangement of this invention is used. The reaction can be terminated simply by removing the displacers from the substrate solutions; the substrate-containing wells can then be simply placed in a standard micro-ELISA reader for the measurement and recording of results. In existing commercial ELISA systems the immunosorbent component (usually the microtitre wells or equivalent) is necessarily a disposable item, but in a system according to this invention, possible covalent attachment or antigens can allow the immunosorbent to be re-usable (if it is desired to be so). The binding reactions can be reversed by soaking the displacers in a releasing agent such as 4M magnesium chloride, or sodium dodecyl sulphate, whilst the covalently attached reagent remains intact. This arrangement can bring benefits in terms of precision, reliability, speed and/or sensitivity. For the manufacturer and user alike there can be important economies in the use of immunoreagents which are often scarce and expensive.

A further optional feature which can be present in the above-described format of this invention is that of the precision heating of individual reaction mixtures. The rates of the binding and of the enzyme/substrate reactions are dependent on temperature; temperature differences across a microtitre plate can cause related response variations, so creating serious defects in calibration and reproducibility. Normally, ELISA reactions are speeded up by placing the tray in a standard air incubator, but this can be less than satisfactory, because the rate at which wells are heated often depends on their position in the tray. The rate of heat exchange in an air incubator is rather slow: the whole plate warms up relatively slowly. Individual heaters can be made (for example, from precision resistance thermometers used in a heating mode rather than a measurement mode), and inserted into the centre of the displacer bodies, for example those illustrated in FIGS. 1–4, and, in that position, can ensure a rapid and efficient delivery of heat through the displacer body surface. This system (which incorporates suitable thermostatic control of a kind well known in itself) can therefore provide faster reactions and reduce well-to-well variation at the same time as dispensing with the need for an incubator.

EXAMPLE 1

An illustrative scheme of preparing materials for immunoassay and carrying out the assay according to the invention is described below, for use with the displacers shown in FIGS. 3–4. The particular assay configuration illustrated happens to be an enzyme-linked antiglobulin test directed to assaying antibodies against soya protein. It will be clear that other configurations and specificities can be used and the arrangements of this invention applied to them, as for example many of those mentioned in U.S. Pat. Nos. 3,654,090, 3,971,932, 3,839,153, 3,850,752, 3,879,262 and 3,996,345.

Preparation of Soya Protein-linked Displacer Pegs

Nylon pegs as described above in relation to FIGS. 3–4 are immersed in 3.6M HCl and held at 48° C. for 35 minutes after which they are washed under running tap water and then soaked in distilled water. Next, they are immersed in chilled 12.5% aqueous glutaraldehyde and kept at 4°–8° C.

for 20 minutes. This reaction is stopped by washing the pegs under running tap water and then soaking them in a large volume of distilled water for at least 2 hours.

After this activation sequence, the pegs are placed in the wells of a microtitre tray, together with 200 µl of a solution of soya protein (300 µg per ml, in phosphate buffered saline with Tween detergent (PBST)+0.1% thimerosal). The trays and pegs are placed in a sealed container and the reaction continued at 37° C. for 54 hours.

Finally, unused active sites are blocked by transferring the pegs into another set of wells containing 200 µl of 1.5M ethanolamine, where they are maintained at room temperature for 24 hours. Before use, they are soaked in PBS+0.15% Tween for a further 3 days at room temperature.

In an alternative preparative method, the hydrolysis and glutaraldehyde treatment are identical but, instead of 300 µg/ml of protein being linked to the surface, the pegs are treated with poly-L-lysine (PLL) at 100 µg/ml for 18 hours at 37° C. After a thorough wash in tap water and then PBST, the linked PLL is activated by treatment with 12.5% glutaraldehyde (18 hours at 37° C.). Finally the soya protein is linked to the glutaraldehyde-substituted PLL by incubating the treated pegs in 200 µl of soya protein at 100 µg/ml, for 18 hours at 37° C. Excess active groups are blocked by treatment in 1.5M ethanolamine at pH 8.5 for seven hours.

In further alternative procedures, the nylon can be treated with dimethyl-1,3-propane diamine to cleave nylon polymer chains, the free amino groups being then substituted with glutaraldehyde, and optionally after further insertion of amino and aldehyde "spacer" groups, the protein desired to be coupled is linked to the terminal aldehyde.

In a further alternative method, not involving polymer chain cleavage of the nylon, displacers are soaked in PBS+ 2% sodium dodecylsulphate and then allowed to dry in the air at room temperature overnight. They are O-alkylated by being immersed in 100% dimethyl sulphate for 3 minutes at room temperature. The reaction is stopped by washing the pegs in ice cold ethanol and then cold water. Immediately thereafter the pegs are immersed in a solution of soya protein (100 µg/ml) and kept at room temperature for 3 days. Finally they are transferred to a 10 mM solution of ethanolamine where they are maintained at room temperature for a further 2 days, before a final wash in Tris/HCl buffer, pH 8.0. Alternatively, the alkylating agent used can be triethyloxonium tetrafluoroborate, as described by Inman and Hornby (1972) cited above. Suitable coupling methods from which choice can be made are mentioned in, for example, GB Specifications 1,316,990, 1,470,955, 1,485,122-3, and U.S. Pat. No. 3,817,837 (cols. 31–34, for example).

Preparation of Enzyme Labelled Sheep-anti Rabbit IgG

Rabbit globulin (prepared from rabbit serum by sodium sulphate precipitation) is immobilised onto cyanogen bromide-activated sepharose 4B (Pharmacia) by the normal procedure described by the manufacturers. A high-titre sheep anti-serum to rabbit globulin (Seward Laboratory, Immunostics (Trade Mark) Product BS 01) is passed down the column and the non-bound fall through fraction rejected. The bound antibodies are released by passing 0.5M acetic acid down the column. The protein-containing fractions are pooled and dialysed against PBS to give an antibody preparation which is conjugated with enzyme by the following procedure.

The following method is based on that described by Engvall and Perlmann (1971) (Immunochemistry, 8, 871). The IgG fraction of sheep antiserum to rabbit IgG (Seward Laboratory, Immunostics (Trade Mark), Product BS 01) is adjusted to a concentration of 5 mg/ml. A 0.1 ml aliquot of this is used to dissolve 1.5 mg of Sigma type VII alkaline phosphatase (supplied as a suspension in 3.2M ammonium sulphate). The resultant solution is dialysed against phosphate buffered saline (PBS) and then mixed with 5 µl of a 25% glutaraldehyde solution (aqueous). The reaction with glutaraldehyde is continued for 2½ hours at room temperature and then stopped by dilution to 1 ml with PBS and extensive dialysis. Finally, the product is diluted to 10 ml in 0.05M tris/HCl buffer (pH 8.0) containing 50 mg/ml ovalbumin, 0.2 mg/ml magnesium chloride, 0.2% sodium azide and 0.2% merthiolate. The conjugate can be applied to a microtitre well bottom by making it concentrated in sucrose solution and a 5–50 microlitre aliquot is then evaporated to a hard sucrose glaze at 37° C. for slow release on stirring.

Preparation of Soya Antigen

The protein used as an antigen is prepared from soya bean flour by a method based on the procedure described by Koh (1978)—Can. Inst. Food Sci. Technol. J., 11, 124. Soya bean flour (10 g) is dispersed in PBS (100 ml) and after thorough mixing the suspension is centrifuged to yield a clear supernatant solution.

An aliquot of this solution is mixed with 30 g of urea to give a final volume of 50 ml. This solution is heated in a steam bath for 1 hour before 1 ml of 2-mercapto-ethanol was added. Steaming is continued for a further 45 minutes. After being cooled to room temperature the solution is dialysed, first against running tap-water for 2 hours and then against 2×5 litres 0.15M sodium chloride. The final dialysed solution swells to 80 ml and has a very slightly opalescent appearance.

Preparation of Rabbit Antibodies to Renatured Soya Protein

Rabbits are given an intra-muscular injection of renatured soya antigen (2 mg) in Freunds' complete adjuvant emulsified as a multiple water-in-oil in water system. The volume given to each animal is 2.0 ml. Subcutaneous booster injections of antigen in saline (0.25–0.5 ml) are given 31, 100, 108 and 115 days after the initial inoculation. Serum samples are taken at various times through this schedule, and used as sources of antibody to be tested for by the following assay schedule.

Immunoassay using the Sensitised (Soya-protein-linked) Displacers

Rabbit antisera and the sheep-anti rabbit/enzyme conjugate are diluted appropriately in PBST and then the following sequence of operations was followed.

1. Diluted antisera placed in wells, followed immediately by sensitised displacer pegs.
2. Displacer pegs+wells (containing a sucrose glaze of conjugate)+sample placed in sealed container and incubated at 37° C. for about 90 minutes. Agitation is carried out but only after about half the incubation period has elapsed.
3. Displacer pegs removed and rinsed under running tap water, then PBST.
4. Washed displacer pegs placed in wells containing substrate for enzyme (Sigma 104 (Trade Mark)).
5. Displacer pegs+wells+substrate placed in a sealed container and incubated at 37° C. for 45 minutes.
6. Displacer pegs removed and optical densities of substrate samples measured.

The standardisation and calibration of this test is carried out by methods which are in themselves well established and form no part of this invention.

EXAMPLE 2

An alternative assay and set of assay materials for the detection or estimation of anti-(soya) antibodies uses a monoclonal antibody. These materials and the assay are carried out as Example 1 except that: A mouse monoclonal anti-(rabbit IgG) with good affinity is used in place of the (polyclonal) sheep antiserum to rabbit IgG previously used. Instead of the IgG fraction of the antiserum prefiously to be mixed with the enzyme and conjugated, an ascitic fluid fraction containing the monoclonal antibody is used: this fraction is prepared by affinity chromatography on the same kind of rabbit globulin-conjugated Sepharose gel as in Example 1, but the elution is carried out afterwards with 4M $MgCl_2$ solution instead of 0.5M acetic acid. The final conjugate preparation is added to the well directly in step 1 instead of being applied as a sucrose glaze, and the incubation time in step 2 can be reduced to 1 hour. It is found that this assay provides not only a gain in time and simplicity but can also yield a more accurate and reliable relationship between final colour development in steps 5–6 and quantity of anti-(soya) antisera added in step 1.

EXAMPLE 3

An assay specific for K-type immunoglobulin G and the preparation of materials for it can be carried out as follows.

Pegs moulded of nylon 66 in the form illustrated in FIG. 3 are washed in alcohol and distilled water. Mouse monoclonal anti-(human K-chain) antibody is immobilised on to them by exposure of the pegs at room temperature for a few hours of overnight to a 20 microgram/ml solution of the antibody in 0.01M aqueous phosphate buffer at pH 8, kept free of other protein and of any detergent. The preparation of monoclonal antibody to K chain (and also of the antibody used below directed to γ-chain) is derived from a corresponding ascitic fluid by affinity chromatography on a column for example of Affigel (Biorad, Trade Mark) conjugated to human IgG, in otherwise the same way as in Example 1 or 2. (About 10 mg IgG is used for conjugation of 1 ml of gel, and at least 2 ml of gel is used for chromatography of 1 ml of ascitic fluid.)

A mouse monoclonal (human γ-chain) antibody is conjugated with alkaline phosphatase as in Example 1, to form the other specific binding reagent in the assay.

The general procedure of Example 1 or 2, was then used together with these materials, except that the non-covalent nature of the absorption of antibody to form immunosorbent made it advisable to use as reaction buffers at pH 7.1 phosphate/saline/Tween/ovalbumin buffer (0.15% phosphate, 0.85% NaCl, 1.5 ml/ml Tween, 1 mg/ml ovalbumin). This provided a specific and sensitive assay for K-type human IgG. An alternative arrangement for the assay of this Example involves omitting the conjugate from step 2, incubating the pegs and test sample about 60 minutes, rinsing, then incubating the pegs about 60 minutes with conjugate dissolved in a similar buffer before going to step 3. Both assay methods give advantage in allowing highly specific determination of the γ-K subpopulation of IgG molecules, because the narrow specificity avoids the interfering cross-reactions which would have rendered such specific assays impossible using less specific reagents.

It was found in one series of trials that the assay result could be made linear in the range 10–100 ng K-IgG per 0.2 ml assay reaction volume, (using about 50 ng conjugate based on starting antibody content).

A corresponding assay for λ-type IgG can be easily carried out if in the preparation of the immunosorbent, i.e. the nylon 66 pegs with antibody immobilised thereon, a mouse monoclonal antibody directed against -chains is used instead.

It can be seen that the particular methods and materials described above can be varied in specificity to provide a wide range of assays sharing the convenience of fewer manipulation steps and freedom from interfering side reactions in use.

Among the monoclonal antibodies that can be obtained according to published procedures and selected for use as assay materials in the present invention are for example anti-rotavirus, anti-(human) IgE, anti-(bovine) IgG, anti-α-fetoprotein, anti-(human and other) IgA, anti-(thyroid-binding globulin), anti-$β_2$ microglobulin, anti-pregnanediol, anti-oestronediol and anti-(human) IgM antibodies, and others. According to the invention these reagents can be used to provide the basis of highly-specific assays for the corresponding specific binding partner which may correspond to the whole population or a specific subpopulation of the type of material under assay: any of the above-described assay procedures are usable for this purpose.

Not all of the corresponding assays need be immunoassays in the strictest sense. For example, using monoclonal anti-(TBG), a corresponding specific binding assay involves immobilised $T_3$ or $T_4$ as the specific binding partner of the TBG being tested for, and the use of a selected marker-conjugated monoclonal anti-TBG enables a sensitive "sandwich" type assay to be carried out in few steps without interference between immune complex formation and the binding of TBG to $T_3$ or $T_4$.

An assay for specific immune complexes can be carried out in an analogous way by the use of immobilised conglutinin and a marker-conjugated monoclonal antibody specific to the component of the immune complexes desired to be assayed.

It will be well understood that the other arrangements of this invention are also susceptible of wide variation application. For example, a set of displacers as shown in FIGS. 3–4 can comprise a handling piece or holder fitted with, e.g., eight pegs, the displacers being appropriately sensitised for use in the assay of human antibodies to any one or more of, for example, toxoplasma, rubella virus, cytomegalovirus and herpesvirus. The displacers can have corresponding antigen fixed thereto, and a marker-conjugated anti-(human globulin) is used in the test which is chemically of the known antiglobulin format, with reagents provided and calibrated accordingly. It can be specially convenient if all four antigen sensitisations are represented in duplicate, each on two displacers of the assembly, shown in FIGS. 3–4. Then such an assembly can, for example, be carried through assay steps designed to assay eight aliquots of a single patient sample, in duplicate for each of the four above-mentioned antibodies. Such an arrangement can be especially convenient in that the remainder of the test tools and reagents, other than the displacers carrying specific sensitisation, can be qualitatively similar for all the assays, for example, the conjugate can be an anti-(human globulin) antibody coupled to a suitable marker enzyme, and common means can be used for detecting the enzyme. These components can be suitably provided in microtitre wells prepared in conjunction with the sensitised displacer pegs, if desired.

Other immunoassay arrangements according to the invention can be directed in specificity towards, for example, immunoglobulin E, (otherwise described as reaginimmunoglobulin), for which an antiglobulin assay can in format resemble the radioimmunoassay using antiglobulin described in U.S. Pat. No. 3,720,760, with optionally the substitution of another kind of marker conjugating the anti-IgE or other labelled antibodies used, e.g. a fluorescent or especially an enzymic marker, used as described above. Where markers other than enzyme markers are used, the appropriate respective known coupling techniques are used. Analogous assay arrangements can be made for clinical diagnostic use, e.g. plasma C-reactive protein, urinary $\beta_2$-microglobulin or Factor VIII. For these antigenic test materials it can be convenient to use a sandwich-type assay format.

Other modifications and variations will be apparent to the skilled reader. In particular, the vesicle-bound marker systems described in specification EP-0014530 can be used to provide marking for the assays of the present invention. Reference is also made to this specification and the literature cited therein for further examples of sandwich and antiglobulin type assay configurations.

We claim:

1. In the process for carrying out a specific binding assay comprising the steps of reacting (a) a sample under assay, possibly containing a substance being tested for, with (b) a specific binding partner for the substance being tested for, immobilised on a solid support, and (c) a specific binding partner for the substance being tested for which is conjugated to a detectable marker, thereby to form a sandwich complex by reaction between whatever quantities are present of the substance being tested for with reagents (b) and (c) and immobilising the marker to the support via the substance being tested for, the marker being detected or assayed as an index of the quantity of the substance being tested for present in the sample (a), the improvement which comprises using reagents (b) and (c) together for reaction with sample (a) and avoiding competitive interference between the binding reactions of the substance being tested for and reagents (b) and (c) by using as reagents (b) and (c), monoclonal antibodies each of narrow and different, non-interfering specificity, the binding reagent (b) being immobilised on the surface of a displacer body which occupies a majority of the volume of a well or cup containing aqueous liquid in which the specific binding reaction takes place.

2. A process according to claim 1, in which the displacer body (2) has a shape substantially complementary to and slightly smaller than that of the well or cup (1), reducing the volume available in the well or cup (1) for occupation by the aqueous reaction liquid by a factor of 2–10.

* * * * *